(12) United States Patent
Panicke et al.

(10) Patent No.: US 7,343,821 B2
(45) Date of Patent: Mar. 18, 2008

(54) DEVICE FOR COUPLING AN ULTRASOUND CLAMP-ON MEASURING HEAD ON THE WALL OF A TUBE

(75) Inventors: Mathias Panicke, Berlin (DE); Bernhard Funck, Rostock (DE)

(73) Assignee: Flexim Flexible Industriemesstechnik GmbH, Berlin (DE)

( * ) Notice: Subject to any disclaimer, the term of this patent is extended or adjusted under 35 U.S.C. 154(b) by 53 days.

(21) Appl. No.: 10/575,647

(22) PCT Filed: Oct. 8, 2004

(86) PCT No.: PCT/EP2004/052482
§ 371 (c)(1),
(2), (4) Date: Jun. 12, 2006

(87) PCT Pub. No.: WO2005/038407
PCT Pub. Date: Apr. 28, 2005

(65) Prior Publication Data
US 2007/0137312 A1     Jun. 21, 2007

(30) Foreign Application Priority Data
Oct. 13, 2003   (DE) ............................... 103 48 083

(51) Int. Cl.
*G01F 1/66*   (2006.01)

(52) U.S. Cl. ..................... 73/861.25; 73/644

(58) Field of Classification Search ...............
73/861.25–861.31, 644
See application file for complete search history.

(56) References Cited

U.S. PATENT DOCUMENTS

| | | | | |
|---|---|---|---|---|
| 3,575,050 | A | * | 4/1971 | Lynnworth ............. 73/861.27 |
| 3,973,152 | A | * | 8/1976 | Karplus ....................... 73/644 |
| 6,047,602 | A | | 4/2000 | Lynnworth |
| 6,349,599 | B1 | | 2/2002 | Lynnworth et al. |

FOREIGN PATENT DOCUMENTS

| | | |
|---|---|---|
| DE | 41 14 233 | 11/1992 |
| DE | 41 24 692 | 1/1993 |

* cited by examiner

*Primary Examiner*—Harshad Patel
(74) *Attorney, Agent, or Firm*—Jordan and Hamburg LLP

(57) ABSTRACT

The invention relates to a device for coupling ultrasound clamp-on throughflow measuring heads to a high-temperature measuring tube. The invention is characterized in that a thin coupling plate is arranged between the tube wall and the measuring head. As a result, the temperature of the measuring head can be reduced to a maximum acceptable value. The shape of the coupling plate affects the adjustable temperature profile in such a way that the isotherms extend in the tube wall area in a parallel manner in relation to the path length of the sound waves in the measuring head area, thereby minimizing resulting errors in throughflow measurement.

12 Claims, 1 Drawing Sheet

DEVICE FOR COUPLING AN ULTRASOUND CLAMP-ON MEASURING HEAD ON THE WALL OF A TUBE

BACKGROUND OF THE INVENTION

The invention relates to an apparatus for acoustic coupling of ultrasound clamp-on flow measuring heads to high-temperature tube lines (greater than 150° C.).

The determination of the flow of liquid and gaseous media is extremely important in industry and metrology. Ultrasound clamp-on systems, such as are described e.g. in DE 41 14 233 C2, work completely intervention-free. In these systems, the two ultrasound measuring heads are fastened to the tube wall from outside and thereby have no direct contact to the measuring medium and do not affect the flow. The angle between sound propagation direction and flow direction of the measuring medium is determined by the law of refraction, the angle of incidence, and by the acoustic velocity of the measuring head. The transitions between the different materials of the measuring head, the tube wall, and the measuring medium run parallel to one another. The ratio of acoustic velocity and sine of the angle of incidence $$\frac{c_i}{\sin\theta_i}$$

corresponding to the law of refraction in all associated media i is the same. The measured flow speed is therefore the proportional to the quotient $$\frac{c_i}{\sin\theta_i}$$

It is established by the material and geometry of the measuring heads and is identified as the sensor constant $$k_\alpha$$

In the aforesaid ultrasound clamp-on flow measurement systems, the measuring heads are coupled directly to the tube wall. The measuring head assumes the temperature of the media and tube due to the direction transmission of heat between tube wall and measuring head. DE 41 24 692 A1 describes a special measuring head that is for use on hot objects and that is characterized by the use of temperature-resistant materials. If the measuring medium and the tube wall have very high temperatures, e.g. greater than 200° C., the measuring head is also correspondingly heated. The severe thermal stress associated with this leads to premature aging in and the inability to function of the measuring heads, e.g. due to depolarization of the piezoceramics that are normally used as transducers. The aforesaid measuring heads for hot objects also do not have the requisite longevity for this stress.

The high-temperature measuring head suggested in U.S. Pat. No. 6,047,602 uses a special waveguide construction for transmitting the ultrasound energy into the measurement tube. This excites shear waves in the waveguide and in the tube wall.

The object of the invention is based on contriving an acoustic coupling that 1. permits a good acoustic coupling between a conventional clamp-on measuring head and the tube wall
2. permits a pronounced difference in temperature between measuring head and tube wall so that the maximum permissible measuring head temperature is not exceeded
3. causes minimal additional measurement errors for the flow speed

SUMMARY OF THE INVENTION

According to the invention, there is provided a coupling plate for coupling an ultrasound measuring head to a conduit wall for measuring flow of a fluid through the conduit. The coupling plate has respective extremities for contacting a surface of the wall of the conduit and the measuring head, respectively, thereby to couple the measuring head to the conduit without contact between the measuring head and the conduit. The coupling plate is so configured that isotherms of the temperature profile of the aforementioned wall surface are substantially parallel to the length of the conduit and, in an area of the plate adjacent the measuring head, are substantially perpendicular to a path of the acoustic beam generated by the measuring head.

The invention is described in the following using exemplary embodiments.

DETAILED DESCRIPTION OF THE INVENTION

Figure 1:
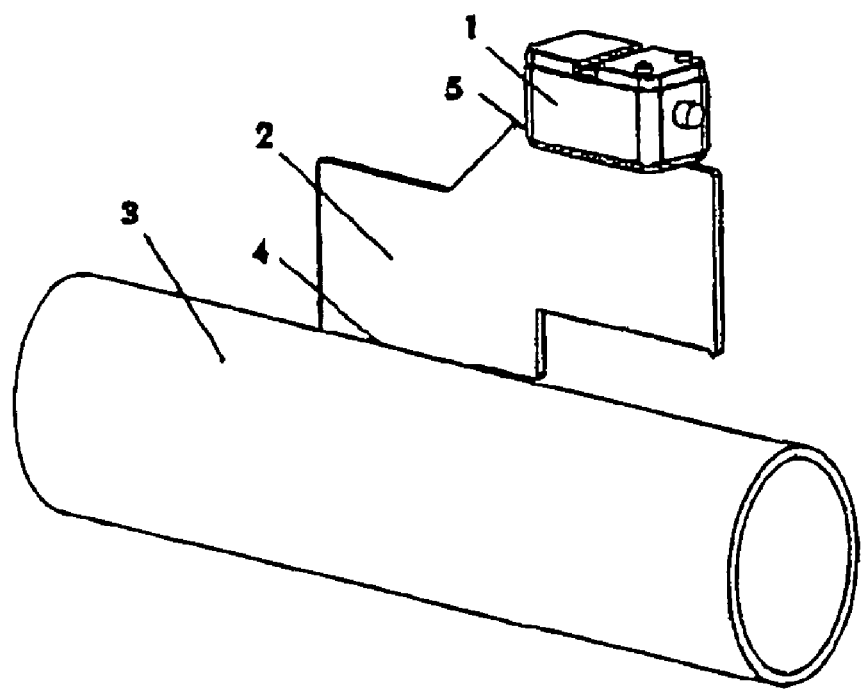
FIG. 1 depicts the coupling plate between measurement tube and clamp-on measuring head.

In accordance with FIG. 1, a specially configured coupling plate 2 is inserted between tube wall 3 and measuring head 1. The coupling plate comprises an acoustically slightly damping material that has low heat conductance, preferably special steel. The thickness is much smaller than the other dimensions of the plate, preferably between 2 and 7 mm. The small surfaces 4 and 5 that act to conduct heat between tube wall 3 and coupling plate 2 and between coupling plate 2 and measuring head 1 admit only a slight heat flow. The heat energy conducted out of the tube therefore remains small. The large lateral surfaces of the coupling plate draw off the majority of the heat that has been fed into the plate. Therefore there is a markedly lower temperature at the measuring head coupling surface 5 than at the tube coupling surface 4, which assumes the temperature of the tube wall. The height of the coupling plate determines the difference in temperature between tube coupling surface and measuring head coupling surface.

The temperature difference between the coupling surfaces leads to a temperature profile within the coupling plate. Due to its thinness, the temperature at all plate depths is nearly the same. The temperature change within the coupling plate is linked to a change in the acoustic velocity. The path length 6 running in the coupling plate is therefore curved.

The quotient that acts for the flow measurement $$\frac{c_{Fluid}}{\sin\theta_{Fluid}}$$

therefore in general is not equal to the sensor constants.

Figure 2:
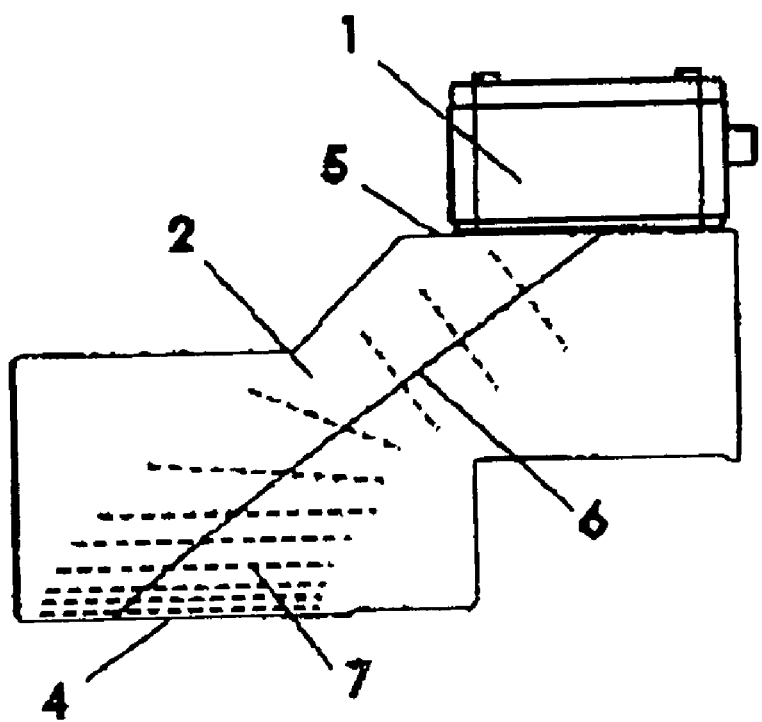
FIG. 2 depicts the temperature course in the coupling plate.

For the special shape of the coupling plate illustrated in FIG. 2, there is a minimum deviation of the effective quotient $$\frac{c_{Fluid}}{\sin\theta_{Fluid}}$$

from the sensor constants. It comprises a largely rectangular area for coupling to the tube that has added to it a largely trapezoidal projection to the measuring head coupling. For limiting the heat added by the tube to the coupling plate, only the area of the coupling plate that is used for the acoustic coupling is in direct contact with the tube wall. The other part of the rectangular area for coupling determines the temperature course in the coupling plate and is offset from the tube wall by a step. An analysis of the temperature course indicates isotherms 7 that are parallel to one another and that run to the tube wall in the rectangular area of the coupling plate. In this area the ratio $$\frac{c_i}{\sin\theta_i}$$

is constant. In the upper diagonally running part of the coupling plate, the acoustic beam runs perpendicular to the isotherms. The acoustic beam is therefore not bent. Overall, the quotient $$\frac{c_i}{\sin\theta_i}$$

that is decisive for the flow measurement is only slightly affected along the entire acoustic beam course in the coupling plate. The difference in temperature to be realized between tube wall and sensor coupling surface determines the height of the coupling plate and the length of the trapezoidal projection. The trapezoidal projection can be omitted if the temperature difference to be attained is slight (70° C.).

The invention claimed is:

1. Apparatus for coupling an ultrasound measuring head to a conduit wall for measuring flow of a fluid through the conduit, comprising
a coupling plate having respective extremities for contacting a surface of said wall and the measuring head, respectively, thereby to couple the measuring head to the conduit without contact between the measuring head and the conduit,
wherein
the coupling plate is so configured that isotherms of temperature profiles of said wall surface are substantially parallel to length of the conduit and, in an area of the plate adjacent the measuring head, are substantially perpendicular to a path of an acoustic beam generated by the measuring head.

2. Apparatus according to claim 1, wherein the coupling plate is substantially comprised of two substantially rectangular areas bounded by three orthogonal edges of the plate, one of said orthogonal edges comprises the plate extremity for contacting said wall surface and areas of the plate remote from said one edge are for not contacting said wall surface.

3. Apparatus according to claim 2, wherein said two substantially rectangular areas are located so as to be offset from each other relative to the length of the conduit.

4. Apparatus according to claim 3, wherein the plate comprises an area interconnecting the two substantially rectangular areas and forming, together with each of said substantially rectangular areas, a substantially trapezoidal area.

5. Apparatus according to any one of claims 1 to 4, wherein thickness of the coupling plate is so selected that temperature of the plate is substantially the same at all plate depths.

6. Apparatus according to claim 5, wherein thickness of the plate is substantially less than width and height of the plate.

7. Apparatus comprising
said coupling plate of claim 1,
an ultrasound measuring head, and
a conduit for conducting therethrough a fluid and through a wall of said conduit flow of the fluid is to be measured by the ultrasound measuring head,
wherein respective extremities of said coupling plate contact said wall of the conduit and the coupling head, respectively, whereby the measuring head is coupled to the conduit without contact between the measuring head and the conduit.

8. Apparatus according to claim 7, wherein the coupling plate is substantially comprised of two substantially rectangular areas bounded by three orthogonal edges of the plate, one of said orthogonal edges comprises the plate extremity for contacting said wall surfaces, areas of the plate remote from said one edge are for contacting said wall surfaces.

9. Apparatus according to claim 8, wherein said two substantially rectangular areas are located so as to be offset from each other relative to the length of the conduit.

10. Apparatus according to claim 9, wherein the plate comprises an area interconnecting the two substantially rectangular areas and forming, together with each of said substantially rectangular areas, a substantially trapezoidal area.

11. Apparatus according to any one of claims 8 to 10, wherein thickness of the coupling plate is so selected that temperature of the plate is substantially the same at all plate depths.

12. Apparatus according to claim 11, wherein thickness of the plate is substantially less than width and height of the plate.

* * * * *